United States Patent
Karlen et al.

[11] Patent Number: 6,156,298
[45] Date of Patent: Dec. 5, 2000

[54] HAIR TREATMENT COMPOSITIONS FOR PROMOTING LUSTER AND STYLABILITY

[75] Inventors: Thomas Karlen, Bern; Daniel Chambettaz, St. Ursen, both of Switzerland; Karin Steinbrecht, Ober-Ramstadt, Germany; Bernhard Irrgang, St. Anton, Switzerland; Michael Franzke, Rossdorf, Germany

[73] Assignee: Wella Aktiengesellschaft, Darmstadt, Germany

[21] Appl. No.: 09/196,037

[22] Filed: Nov. 19, 1998

[30] Foreign Application Priority Data

Nov. 29, 1997 [DE] Germany .............. 197 53 108

[51] Int. Cl.⁷ ...................................... A61K 7/11
[52] U.S. Cl. ........................................ 424/70.31; 424/70.1
[58] Field of Search .................. 424/70.31, 70.1

[56] References Cited

U.S. PATENT DOCUMENTS

| | | | |
|---|---|---|---|
| 4,869,900 | 9/1989 | Pozzi et al. | 424/94.1 |
| 5,326,755 | 7/1994 | Blade et al. | |
| 5,371,251 | 12/1994 | Hamann et al. | 554/97 |
| 5,525,263 | 6/1996 | Bimczok et al. | 252/551 |
| 5,597,551 | 1/1997 | Malawer et al. | |
| 5,626,835 | 5/1997 | Malawer et al. | |
| 5,980,876 | 11/1999 | Peffly | 424/70.12 |
| 5,993,792 | 11/1999 | Rath et al. | 424/70.28 |

FOREIGN PATENT DOCUMENTS

| | | |
|---|---|---|
| 0 445 659 A2 | 9/1991 | European Pat. Off. . |
| 0 568 035 A2 | 11/1993 | European Pat. Off. . |
| 42 30 876 A1 | 9/1993 | Germany . |

OTHER PUBLICATIONS

International Cosmetic Ingredient Dictionary, Fifth Edition, vol. 1 (Cosmetic, Toiletry, and Fragrance Association 1993).
Ruth Winter, M.S., A Consumer's Dictionary of Cosmetic Ingredients, Fifth Edition (Three Rivers Press 1999).

*Primary Examiner*—Thurman K. Page
*Assistant Examiner*—P. E. McQueeney
*Attorney, Agent, or Firm*—Michael J. Striker

[57] ABSTRACT

The hair treatment composition for promoting luster and stylability of hair consists of an aqueous or aqueous-alcoholic solution containing preferably from 0.1 to 30 percent by weight of at least one fatty acid glyceride polyalkylene glycol ether having from 70 to 1000 alkylene glycol units or at least one fatty acid partial glyceride polyalkylene glycol ether having from 70 to 1000 alkylene glycol units and a propellant which is dimethyl ether and/or a volatile hydrocarbons or a mixture of volatile hydrocarbons so that the hair treatment composition consists of a single-phase aerosol preparation. The composition is composed so that an aerosol foam is formed on the hair when the hair treatment composition is applied to the hair.

10 Claims, No Drawings

HAIR TREATMENT COMPOSITIONS FOR PROMOTING LUSTER AND STYLABILITY

BACKGROUND OF THE INVENTION

1. Field of the Invention

The present invention relates to a composition for promoting or increasing hair luster and stylability and, more particularly, to a composition for promoting or increasing hair luster and stylability containing a fatty acid glyceride polyalkylene glycol ether or a fatty acid partial glyceride polyalkylene glycol ether having 30 to 1000 alkylene glycol units and a propellant.

2. Prior Art

Research and development in the hair treatment composition field has already provided preparations in the form of pomades that provide easy shaping and increased luster and hold of the hair style. Normally hydrocarbons (e.g. paraffins), silicone oils or surfactants with a reduced HLB-value are used for the purpose of producing style-improving and luster-improving properties. The stabilization of these kinds of pomades is a problem, because they are inclined to separate into an aqueous phase and lipophilic phase. Furthermore, decomposition of the, silicone oils is difficult.

It is also possible to use common soluble nonionic surfactants, for example fatty alcohol ethoxylates and fatty acid ethoxylates, as luster and fixing providing agents. In order to provide these nonionic surfactants with sufficient water-solubility, they must be present in highly ethoxylated form. To obtain a sufficiently strong pomade effect, however a sufficient amount of a highly ethoxylated nonionic surfactant must be used, which is expensive. Furthermore highly ethoxylated nonionic surfactants are inclined to be waxy or solid in the water-free state and that results in the formation of a solid dry film after application to the hair and after a drying stage, which produces an unpleasant hard hair feel and insufficient hair pliability.

The form of the usually administered pomades is predominantly limited to non-transparent creamy emulsions. These creamy emulsions often have a poor distributability on hair so that hair fixing or styling is difficult. Application of a pomade is often improved if the pomade is applied to the hair in the form of an aerosol-foam, which breaks down in the hair when it is worked into the hair or when the hair is set in a hair style.

However it is disadvantageous that this goal can be achieved with the currently used hair treatment compositions only in the form of preparations that separate into an aqueous part and a propellant part in the usual time of one to two days between two applications. Because of that the preparation of a single-phase product with the suitable convenience advantages for the user has been difficult. A strong increase of the amount of the emulsifier leads of course to the desired single-phase product however this product is expensive and loads the hair strongly. The use of a large proportion of non-aqueous solvents, such as alcohols with one to eight carbon atoms, glycerol, propylene glycol or the soluble propellant gas dimethylether drastically degrades the foaming properties.

SUMMARY OF THE INVENTION

It is an object of the present invention to provide a composition for promoting or increasing hair luster and stylability of the above-described kind that does not have the above-described disadvantages.

This object is attained by the use of a special, highly ethoxylated nonionic surfactant compound that leads to a composition that may be outstandingly worked into the hair and imparts good shapability or stylability and long lasting luster to the hair, even in reduced amounts in an aerosol preparation.

The hair treatment composition according to the invention contains (A) at least one fatty acid glyceride polyalkylene glycol ether or at least one fatty acid partial glyceride polyalkylene glycol ether having 30 to 1000 alkylene glycol units, and (B) at least one propellant that is soluble or insoluble in water.

The invention also includes the use of a fatty acid glyceride polyalkylene glycol ether or a fatty acid partial glyceride polyalkylene glycol ether having 30 to 1000 alkylene glycol units to make a composition for improvement of the shapability or stylability and the luster of hair.

The term "partial glyceride" means monoglycerides or diglyceride or a mixture of monoglycerides and diglycerides.

Ingredient (A) preferably is a compound of the general formula (I):

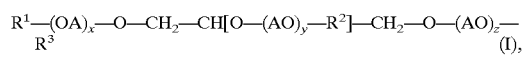

$$R^1-(OA)_x-O-CH_2-CH[O-(AO)_y-R^2]-CH_2-O-(AO)_z-R^3 \quad (I),$$

wherein $R^1$, $R^2$ and $R^3$ are each, independently of each other, H, saturated or unsaturated branched or unbranched unsubstituted $C_6$- to $C_{22}$-acyl groups or saturated or unsaturated branched or unbranched substituted $C_6$- to $C_{22}$-acyl groups having one or more hydroxy group substituent; wherein at least one of the substituents $R^1$, $R^2$ and $R^3$ is a $C_6$- to $C_{22}$-acyl group; A is an alkylene group with two or three carbon atoms; x, y and z are whole numbers between 0 and 1000, wherein the sum x+y+z is between 30 and 1000, preferably from 30 to 500, especially preferably between 70 and 250. In particularly preferred compounds of formula (I) $R^1$ is H, $R^2$ is H or a $C_6$- to $C_{22}$-acyl group and $R^3$ is a $C_6$- to $C_{22}$-acyl group, A is an ethylene group and x and y are both 0.

Examples of suitable compounds for component (A) include polyethylene glycol(30)-glyceryl cocoate, polyethylene glycol(80)-glycerylcocoate, polyethylene glycol(80)-glyceryl tallowate, polyethylene glycol(120)-glyceryl stearate, polyethylene-glycol(200)-glyceryl stearate, polyethylene glycol(200)-glyceryl tallowate and hydrogenated polyethylene glycol(200)-gylceryl palmitate. The hydrogenated polyethylene glycol(200)-glyceryl palmitate is especially preferred.

The composition according to the invention preferably contains from 0.1 to 30 percent by weight of component (A), especially preferably from 0.3 to 20 or 0.5 to 12 percent by weight.

Preferred water-soluble propellants include volatile hydrocarbons, such as propane and butane and their mixtures and fluorinated propellants. Dimethyl ether is particularly preferred as the water-soluble propellant.

The composition according to the invention is preferably in the form of an aqueous or an aqueous-alcoholic solution and in the form of a single-phase aerosol composition. The viscosity of the solution is preferably less than 100 mm²/s at 20° C. The lower alcohols having from one to four carbon atoms that are conventionally used for cosmetic purposes, for example ethanol or isopropanol, are preferred as alcohols for use in the compositions according to the invention. Furthermore solvents with a boiling point under 600° C. can also be used. Propylene glycols and glycerol are particularly preferred. The solvent is preferably present in the composition of the invention in an amount of from 0.01 to 50 percent by weight, especially preferably in an amount of from 2 to 30 percent by weight.

The composition according to the invention can also contain water-insoluble solvents, for example branched or unbranched hydrocarbons, such as pentane, hexane, isopentane and cyclic hydrocarbons, such as cyclopentane and cyclohexane. Paraffins and isodecanes are particularly preferred.

The composition according to the invention can also contain at least one additional nonionic surfactant compound preferably in an amount of from 0.1 to 30 percent by weight, especially preferably from 0.5 to 20 percent by weight, as an additional component (C).

Preferred nonionic surfactant compounds include ethoxylated fatty acids with 10 to 26 carbon atoms, ethoxylated alcohols, ethoxylated fatty alcohols with 10 to 26 carbon atoms, ethoxylated hydrogenated or non-hydrogenated castor oil, glyceride alkoxylates, fatty acid glyceride polyalkylene glycol ethers or fatty acid partial glyceride polyalkylene glycol ethers with less than 30 alkylene glycol units respectively, such as polyethylene glycol(7)-glyceryl cocoate, polyglycolamides, fatty acid sugar esters, ethoxylated fatty acid sugar esters and alkyl polyglycosides. The ethoxylation degree of the ethoxylated surfactant compound is preferably greater than 3.

Suitable ethoxylated fatty acids include, for example, polyethylene glycol(75)-laurate, polyethylene glycol(90)-stearate, polyethylene glycol(120)-stearate, polyethylene glycol(120)-polypropylene glycol-stearate, polyethylene glycol(150)-dilaurate or polyethylene glycol(175)-distearate.

Suitable ethoxylated fatty acid sugar esters include ethoxylated sorbitan fatty acid esters or polyethylene-glycol (120)-methylglucose dioleate.

The composition according to the invention can also contain at least one film-forming, hair-fixing polymer preferably in an amount of from 0.01 to 10 percent by weight, especially preferably from 0.1 to 8 percent by weight as an another additional component (D). The polymer can be of synthetic or natural origin and can be nonionic, anionic, cationic or amphoteric. The hair fixing polymers can be used individually or in a mixture.

The term "film-forming, hair-fixing polymer" here means those polymers which in a 0.1 to 5 percent aqueous, alcoholic or aqueous-alcoholic solution are in a position to deposit a polymer film on the hair and in this way to fix the hair.

Suitable synthetic, nonionic, film-forming, hair-fixing polymers for use in the compositions of the invention can include homopolymers of vinyl pyrrolidones, homopolymers of N-vinyl formamides, copolymers of vinyl pyrrolidiones and dimethylaminomethylmethacrylates, copolymers of vinyl pyrrolidiones and dimethylaminoethylmethacrylates, copolymers of vinyl pyrrolidiones and dimethylaminopropylmethacrylates, copolymerizates of vinyl pyrrolidone and vinyl acetate, terpolymers of vinyl pyrrolidone, vinyl acetate and vinyl propionate, polyacrylamides, polyvinyl alcohols or polyethylene glycol/polypropylene glycol compolymers.

Suitable synthetic film-forming anionic polymers are, for example, crotonic acid/vinyl acetate copolymers, vinyl pyrrolidone/vinyl acrylate copolymer, terpolymers of acrylic acid, ethyl acrylate and N-t-butylacrylamide and methyl vinyl ether/maleic acid anhydride copolymers and their monoesters.

Natural film-forming polymers or derivatives thereof made by chemical reactions can also be used in the hair treatment compositions of the invention. Well-tested examples of these ingredients for the hair treatment compositions include low molecular weight or high molecular weight chitosan with a molecular weight of from 20,000 to three million g/mol, polysaccharides or mixture made from oligo-, mono- and disaccharides (C-Pur© 01924 of Cerestar), Chinese balsam word (Kolophonium), cellulose derivatives, such as hydroxypropyl cellulose with a molecular weight of from 30,000 to 50,000 g/mol, or shellac in neutralized or unneutralized form.

Amphoteric polymers can also be used in the composition according to the invention. These amphoteric polymers either have both free acid groups, such as carboxylic acid or sulfonic acid groups, and free basic groups, such as amino groups, or contain both cationic groups, such as quaternary ammonium groups, and anionic groups, such as carboxylate or sulfate or sulfonate groups. Copolymers such as octyl acrylamides, t-butylaminoethylmethacrylate and two or more monomers from the group consisting of acrylic acids, methacrylic acids and their simple esters are especially suitable.

According to the invention the cationic polymers used in the invention can carry the cationic groups either in a side chain or in the polymer chain backbone. Quaternary nitrogen atoms can carry four different substituents or substituents that are in part the same or can be part of a ring system. Preferred cationic groups include ammonium or imidazolinium groups. The cationic polymers are preferably copolymerizates with nonionic polymerizable vinyl monomers, especially vinyl pyrrolidone, vinyl acetate, acrylamide, methacryl amide, methacrylate, ethyl acrylate, methyl metacrylate or ethyl methacrylate. The principal polymer chain can however also be derived from glycosides or proteins.

Suitable cationic polymers include, for example, copolymers of vinyl pyrrolidones with quaternary derivatives of dialkylaminoethylacrylates or -methacrylates, copolymerizates of vinylpyrrolidones with vinylimidazolium methochloride, polymers of dimethyldiallyl ammonium salts and their copolymers with esters or amides of acrylic or methacrylic acids, condensate resin made from polyglycols and polyamines, cationic derivatives of silicone oils, cationic derivatives of protein hydroylzates and quaternary cellulsoe or guar derivative compounds.

These polymers include the quaternary vinyl pyrrolidone/dimethylaminoethylmethacrylate copolymer with diethylsulfate, the copolymerizate of vinyl pyrrolidone with vinyl imidazolium methochloride, the terpolymer of dimethyldiallyl ammonium chloride, sodium acrylate and acrylamide, the terpolymer of vinyl pyrrolidone, dimethylaminoethylmethacrylate and vinyl caprolactam, the quaternarized ammonium salt, made from hydroxyethyl cellulose and an epoxide substituted with trimethyl ammonium, the vinyl pyrrolidone/methacrylamido-propyltrimethyl ammonium chloride copolymer and diquaternary polydimethylsiloxane.

Furthermore polymers with a thickener action can be used, in as much as they are compatible with the composition according to the invention. Thus for example homopolymers of acrylic acid with a molecular weight of from 2,000,000 to 6,000,000 g/mol are suitable. Also copolymers made from acrylic acid an acryl amide (sodium salt) with a molecular weight of from 2,000,000 to 6,000,000 g/mol and sclerotium gum are suitable. Copolymers of acrylic acid and methacrylic acid and copolymers of acrylates and/or methacrylate monomers and acrylate- or methacrylate esters ethoxylated $C_1$- to $C_{30}$-alcohols, such as acrylate/steareth-20 methacrylate copolymers or steareth-10 allyl ether/acrylate copolymers.

The above-mentioned thickened or film-forming anionic or amphoteric polymers can be partially or entirely neutralized with organic or inorganic bases. Preferred bases include particularly primary and secondary amines, such as aminoethylpropanol. Cationic polymers, which contain basic groups, can be partially or completely neutralized with organic or inorganic acids.

Furthermore the compositions according to the invention can contain water-soluble or water-insoluble silicone compounds in a concentration of from 0.01 to 50 percent by weight, preferably in a concentration of from 0.1 to 5 percent by weight. Volatile and nonvolatile cyclomethicones, dimethicones and dimethicone copolyols are particularly preferred. Examples of these compounds include polydimethylsiloxane (INCI: dimethicone), α-hydro-ω-hydroxypolyoxydimethylsilylene (INCI:dimethiconol), cyclic dimethylpolysiloxane (INCI:cyclomethicone), trimethyl-(octadecyloxy)silane (INCI: stearoxytrimethylsilane), dimethylsiloxane-glycol copolymer (INCI: dimethicone copolyol), dimethylsiloxane/aminoalkylsiloxane copolymer with hydroxy end groups (INCI: amodimethicone), monomethyl-polysiloxane with lauryl side chains (INCI: laurylmethicone copolyol), dimethylsiloxane glycol copolymer acetate (INCI: dimethicone copolyol acetate) and dimethylsiloxane aminoalkyl siloxane copolymer with trimethylsilyl end groups (INCI: trimethylsilylamodimethicone). Preferred silicone polymers include dimethicones, which for example is marketed under the trade name Siloxane F-221 by Wacker, Munich, Germany or by Dow Corning, Europe under the trade name Dow Corning Fluid 200/0.65; cyclomethicones, which for example are marketed under the trade name Dow Corning 244 by Dow Corning, Europe or Abil® K4 by Goldschmidt; and dimethiconols, which are marketed, for example, under the trade name Silicone Fluid F-212 by Wacker or Unisil SF-R by UPI.

The names given in parentheses above correspond to the INCI nomenclature (International Cosmetic Ingredients), as defined for cosmetic effective and auxiliary materials.

Mixtures of silicone polymers are also suitable, such as a mixture of dimethicone and dimethiconol, which for example is marketed under the trade name Dow Corning 1403 Fluid of Dow Corning Europe.

Additional suitable silicone polymers include dimethicone copolyols, which are marketed under the tradename Surfactant 193 of Dow Corning, Europe or Silwet® of Union Carbide; amodimethicones, which for example are sold under the tradename Sandoperm® FE of Sandoz or SM 2059 of General Electric, U.S.A.; lauryl methicone copolyol, which is sold under the trade name Dow Corning Q2-5200 of Dow Corning, Europe; trimethylsilylamodimethicones, which are sold under the tradename Dow Corning Q2-8220 of Dow Corning, Europe or Silicone Fluid F-801 of Wacker; dimethicone copolyol acetate, which is marketed under the trade name Silicone Fluid VP or Belsil® DMC 6033 of Wacker and trimethyl-(octadecyloxy)silane (INCI: stearoxytrimethylsilane), which is sold, for example, under the trade name Dow Corning 580 WAX of Dow Corning, Europe.

The composition according to the invention can contain a consistency provider, such as are conventionally used for creams, for example fatty alcohols and fatty alcohol sulfates as sold under the trademark Lanette®. Similarly polyethylene glycols that are liquid, waxy or solid at room temperature can be contained in the compositions of the invention.

Understandably the composition according to the invention can contain conventional cosmetic additive ingredients, such as non-fixing, non-ionic polymers, non-fixing, anionic polymers and non-fixing, natural polymers and their combinations in an amount of preferably from 0.01 to 15 percent by weight; perfume oils in an amount of preferably from 0.01 to 5 percent by weight; turbidity-inducing agents, such as ethylene glycol distearate, styrene/PVP copolymers or polystyrenes in an amount of preferably from 0.01 to 5 percent by weight; wetting agents, surfactants or emulsifiers with or without washing activity selected from the classes of anionic, cationic and amphoteric surface-active compounds, such as fatty alcohol sulfates, fatty alcohol ether sulfates and fatty acid alkanol amides, preferably in an amount of from 0.1 to 20 percent by weight; further moisturizers, dye compound, light protective agents, antioxidants, luster-giving agents and preservatives in an amount of preferably from 0.01 to 10 percent by weight.

The composition according to the invention is characterized by remaining stable for a longer time, transparent to mildly opaque emulsions with water-insoluble materials, such as hydrocarbons or silicone oils, and forms a fine-pored, easily distributed foam on dispensing which breaks down when worked into the hair. The composition according to the invention provides an improvement in shaping or hair styling and a long lasting luster and soft feel to the hair.

The following examples serve to illustrate the composition of the invention without limiting the appended claims.

EXAMPLES

Example 1
Hair Treatment Composition for Easy Styling

| | |
|---|---|
| 0.75 g | hydrogenated polyethylene glycol(200)-glyceryl palmitate |
| 0.25 g | polyethyleneglycol(7)-glyceryl cocoate |
| 9.0 g | hydrogenated castor oil, ethoxylated with 40 mol of ethylene oxide |
| 84.0 g | water |
| 6.0 g | dimethyl ether |
| 100.00 g | |

Example 2
Hair Treatment Composition for Easy Styling

| | |
|---|---|
| 5.25 g | hydrogenated polyethylene glycol(200)-glyceryl tallowate |
| 1.75 g | polyethyleneglycol(7)-glyceryl cocoate |
| 87.0 g | water |
| 6.0 g | dimethyl ether |
| 100.00 g | |

Example 3
Hair Treatment Composition with Care-giving Effect

| | |
|---|---|
| 0.7 g | hydrogenated polyethylene glycol(200)-glyceryl palmitate |
| 9.0 g | hydrogenated castor oil, ethoxylated with 35 mol of ethylene oxide |
| 3.0 g | cetyltrimethylammonium chloride |
| 1.0 g | acrylate/steareth-20 methacrylate copolymer (Acrysol ® 22), with aminomethylpropanol neutralized to pH = 7 |

-continued

| | |
|---|---|
| 84.3 g | water |
| 2.0 g | propane/butane, 2.7 bar |
| 100.00 g | |

Example 4
Hair Treatment Composition with Care-giving Effect

| | |
|---|---|
| 5.25 g | hydrogenated polyethylene glycol(200)-glyceryl palmitate |
| 1.75 g | polyethyleneglycol(7)-glyceryl cocoate |
| 0.9 g | hydrogenated castor oil, ethoxylated with 35 mol of ethylene oxide |
| 0.3 g | glucose decyl ether |
| 1.0 g | amodimethicone |
| 84.8 g | water |
| 6.0 g | dimethyl ether |
| 100.00 g | |

Example 5
Hair Treatment Composition for Providing Improved Luster

| | |
|---|---|
| 7.0 g | polyethylene glycol(200)-glyceryl stearate |
| 9.0 g | hydrogenated polyethylene glycol(35) castor oil |
| 1.0 g | polyethylene glycol(4)-lauryl ether |
| 1.0 g | silicone oil AK 500 |
| 74.0 g | water |
| 6.0 g | dimethyl ether |
| 2.0 g | propane/butane, 2.7 bar |
| 100.00 g | |

Example 6
Hair Treatment Composition for Providing Improved Luster and Protection for the Hair

| | |
|---|---|
| 5.25 g | polyethylene glycol(200)-glyceryl tallowate |
| 1.75 g | polyethylene glycol(7)-glyceryl cocoate |
| 9.0 g | hydrogenated polyethylene glycol(35) castor oil |
| 1.0 g | polyethylene glycol(4)-lauryl ether |
| 1.0 g | dimethiconol, 13% in cyclomethicone (Dow Corning 1401 Fluid) |
| 0.3 g | acrylate/C10–30 alkylacrylate crosspolymer (Pemulen ® TR-1, Goodrich) |
| 73.7 g | water |
| 6.0 g | dimethyl ether |
| 2.0 g | propane/butane, 2.7 bar |
| 100.00 g | |

Example 7
Hair Treatment Composition for Providing Improved Luster and for Moisturizing

| | |
|---|---|
| 7.0 g | polyethylene glycol(30)-glyceryl cocoate |
| 10.0 g | propylene glycol |

-continued

| | |
|---|---|
| 75.0 g | water |
| 2.0 g | propane/butane, 2.7 bar |
| 6.0 g | dimethyl ether |
| 100.00 g | |

Example 8
Hair Treatment Composition with Rapid Drying Effect

| | |
|---|---|
| 7.0 g | polyethylene glycol(80)-glyceryl cocoate |
| 20.0 g | ethanol |
| 65.0 g | water |
| 2.0 g | propane/butane, 2.7 bar |
| 6.0 g | dimethyl ether |
| 100.00 g | |

Example 9
Hair Treatment Composition with Rapid Drying Effect

| | |
|---|---|
| 7.0 g | polyethylene glycol(80)-glyceryl talloate |
| 9.0 g | hydrogenated castor oil, ethoxylated with 40 mol of ethylene oxide |
| 20.0 g | ethanol |
| 56.0 g | water |
| 2.0 g | propane/butane, 2.7 bar |
| 6.0 g | dimethyl ether |
| 100.00 g | |

Example 10
Hair Treatment Composition with UV Protection

| | |
|---|---|
| 0.5 g | polyethylene glycol(200)-glyceryl stearate |
| 9.0 g | hydrogenated castor oil, ethoxylated with 40 mol of ethylene oxide |
| 0.5 g | polyoxyethylene(25)-p-aminobenzoic acid |
| 82.0 g | water |
| 2.0 g | propane/butane, 2.7 bar |
| 6.0 g | dimethyl ether |
| 100.00 g | |

Example 11
Hair Treatment Composition with Hair Fixing Effect

| | |
|---|---|
| 7.0 g | hydrogenated polyethylene glycol(200)-glyceryl palmitate |
| 0.2 g | polyoxyethylene(120)-methylglucosedioleate |
| 4.0 g | polyvinyl pyrrolidone (Luviskol ® K 60, BASF) |
| 80.8 g | water |
| 2.0 g | propane/butane, 2.7 bar |
| 6.0 g | dimethyl ether |
| 100.00 g | |

Example 12
Hair Treatment Composition with Hair-fixing Effect

| | |
|---|---|
| 5.25 g | hydrogenated polyethylene glycol(200)-glyceryl palmitate |
| 1.75 g | polyethyleneglycol(7)-glyceryl cocoate |
| 0.3 g | polyethyleneglycol(23)-lauryl ether |
| 2.0 g | vinyl acetate/crotonate copolymer (Luviset ® CA-66, BASF) |
| 82.7 g | water |
| 2.0 g | propane/butane, 2.7 bar |
| 6.0 g | dimethyl ether |
| 100.00 g | |

Example 13
Hair Treatment Composition with Fixing Effect

| | |
|---|---|
| 7.0 g | polyethylene glycol(80)-glyceryl talloate |
| 4.0 g | vinyl pyrrolidone/dimethylaminoethyl-methacrylate methosulfate copolymer, 20% in water (Gafquat ® 755 N, ISP) |
| 81.0 g | water |
| 2.0 g | propane/butane, 2.7 bar |
| 6.0 g | dimethyl ether |
| 100.00 g | |

Example 14
Hair Treatment Composition with Fixing Effect

| | |
|---|---|
| 5.25 g | hydrogenated polyethylene glycol(200)-glyceryl talloate |
| 1.75 g | polyethylene glycol(7)-glyceryl cocoate |
| 9.0 g | hydrogenated castor oil, ethoxylated with 40 mol of ethylene oxide |
| 1.0 g | octylacrylamide/acrylate/butylaminoethyl-methacrylate copolymer (Amphomer ®, National Starch) |
| 75.0 g | water |
| 2.0 g | propane/butane, 2.7 bar |
| 6.0 g | dimethyl ether |
| 100.00 g | |

Example 15
Hair Treatment Composition with Fixing Effect

| | |
|---|---|
| 5.25 g | hydrogenated polyethylene glycol(200)-glyceryl talloate |
| 1.75 g | polyethylene glycol(7)-glyceryl cocoate |
| 9.0 g | hydrogenated castor oil, ethoxylated with 40 mol of ethylene oxide |
| 0.6 g | chitosan |
| 75.4 g | water |
| 2.0 g | propane/butane, 2.7 bar |
| 6.0 g | dimethyl ether |
| 100.00 g | |

Example 16
Hair Treatment Composition with Conditioning Polymer

| | |
|---|---|
| 5.25 g | hydrogenated olyethylene glycol(200)-glyceryl palmitate |
| 1.75 g | polyethylene glycol(7)-glyceryl cocoate |
| 0.3 g | hydroxypropyl-guar-hydroxypropyltrimethyl-ammonium chloride (Jaguar ® C162, Rhone-Poulenc) |
| 84.7 g | water |
| 2.0 g | propane/butane, 2.7 bar |
| 6.0 g | dimethyl ether |
| 100.00 g | |

Example 17
Hair Treatment Composition with Skin Calming Effect

| | |
|---|---|
| 7.0 g | polyethylene glycol(30)-glyceryl cocoate |
| 1.0 g | Chamomile extract |
| 84.0 g | water |
| 2.0 g | propane/butane, 2.7 bar |
| 6.0 g | dimethyl ether |
| 100.00 g | |

The disclosure in German Patent Application 197 53 108.3-41 of Nov. 29, 1997 is incorporated here by reference. This German Patent Application describes the invention described hereinabove and claimed in the claims appended hereininbelow and provides the basis for a claim of priority for the instant invention under 35 U.S.C. 119.

While the invention has been illustrated and described as embodied in hair treatment compositions for promoting luster and stylability, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A hair treatment composition for promoting luster and stylability of hair,
   wherein said hair treatment composition consists of an aqueous or aqueous-alcoholic solution and said solution comprises
      at least one fatty acid glyceride polyalkylene glycol ether having from 30 to 1000 alkylene glycol units or at least one fatty acid partial glyceride polyalkylene glycol ether having from 30 to 1000 alkylene glycol units; and
      at least one propellant selected from the group consisting of dimethyl ether and volatile hydrocarbons; and
   wherein said hair treatment composition consists of a single-phase aerosol preparation, whereby an aerosol foam is formed on the hair when the hair treatment composition is applied to the hair.

2. The hair treatment composition as defined in claim 1, wherein said at least one fatty acid glyceride polyalkylene glycol ether or said at least one fatty acid partial glyceride polyalkylene glycol ether is a compound of formula (I):

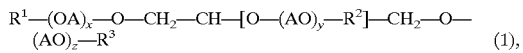

(1), wherein $R^1$, $R^2$ and $R^3$ are each, independently of each other, selected from the group consisting of H and $C_6$- to $C_{22}$-acyl groups, with the proviso that at least one of the substituents $R^1$, $R^2$ and $R^3$ is one of said $C_6$- to $C_{22}$-acyl groups; A is an alkylene group with two or three carbon atoms, x, y and z are whole numbers between 0 and 1000, and the sum x+y+z is between 30 to 1000.

3. The hair treatment composition as defined in claim 2, wherein said $R^1$ is said H, said $R^2$ is said H or one of said $C_6$- to $C_{22}$-acyl groups, said $R^3$ is said one of said $C_6$- to $C_{22}$-acyl groups or another of said $C_6$- to $C_{22}$-acyl groups, said A is an ethylene group and said x and y are both 0.

4. The hair treatment composition as defined in claim 1 or 2, wherein said at least one fatty acid glyceride polyalkylene glycol ether have from 70 to 1000 of said alkylene glycol units or said at least one fatty acid partial glyceride polyalkylene glycol ether have from 30 to 1000 of said alkylene glycol units.

5. The hair treatment composition as defined in claim 1, wherein said at least one fatty acid glyceride polyalkylene glycol ether or said at least one fatty acid partial glyceride polyalkylene glycol ether is hydrogenated glyceryl palmitate with about 200 polyethylene glycol units.

6. The hair treatment composition as defined in claim 1, containing from 0.1 to 30 percent by weight of said at least one fatty acid glyceride polyalkylene glycol ether or said at least one fatty acid partial glyceride polyalkylene glycol ether.

7. The hair treatment composition as defined in claim 1, having a viscosity of less than 100 mm$^2$/s at 20° C.

8. The hair treatment composition as defined in claim 1, further comprising from 0.1 to 30 percent by weight of at least one nonionic surfactant compound selected from the group consisting of ethoxylated fatty acids, ethoxylated alcohols, ethoxylated fatty alcohols, glyceride alkoxylates, fatty acid glyceride polyalkylene glycol ethers with less than 30 alkylene glycol units, fatty acid partial glyceride polyalkylene glycol ethers with less than 30 alkylene glycol units, polyglycolamides, fatty acid sugar esters, ethoxylated fatty acid sugar esters and alkylpolyglycosides.

9. The hair treatment composition as defined in claim 1, further comprising from 0.01 to 10 percent by weight of a film-forming hair-fixing polymer.

10. A method of treating hair to improve hair luster and stylability, said method comprising the steps of:

a) providing a hair treatment composition consisting of an aqueous or aqueous-alcoholic solution, at least one fatty acid glyceride polyalkylene glycol ether having from 30 to 1000 alkylene glycol units or at least one fatty acid partial glyceride polyalkylene glycol ether having from 30 to 1000 alkylene glycol units; and at least one propellant selected from the group consisting of dimethyl ether and volatile hydrocarbons, said hair treatment compositions consisting of a single-phase aerosol preparation;

b) applying the hair treatment composition of step a) to the hair.

* * * * *